United States Patent
Yu et al.

(10) Patent No.: US 6,943,244 B2
(45) Date of Patent: Sep. 13, 2005

(54) HUMAN G-TYPE LYSOZYME, THE ENCODING SEQUENCE, PREPARING METHOD AND THE USES THEREOF

(75) Inventors: Long Yu, Institute of Genetics, Fudan University, 220 Handan Road, Shanghai (CN), 200433; Yong Zhao, Shanghai (CN); Peirong Hu, Shanghai (CN); Lisha Tang, Shanghai (CN); Shouyuan Zhao, Shanghai (CN)

(73) Assignee: Long Yu, Shanghai (CN)

( * ) Notice: Subject to any disclaimer, the term of this patent is extended or adjusted under 35 U.S.C. 154(b) by 169 days.

(21) Appl. No.: 10/469,602

(22) PCT Filed: Jul. 17, 2001

(86) PCT No.: PCT/CN01/01176

§ 371 (c)(1),
(2), (4) Date: Sep. 2, 2003

(87) PCT Pub. No.: WO02/070715

PCT Pub. Date: Sep. 12, 2002

(65) Prior Publication Data

US 2004/0072292 A1 Apr. 15, 2004

(30) Foreign Application Priority Data

Mar. 2, 2001 (CN) .......................................... 1105523 A

(51) Int. Cl.[7] ........................ C12N 15/56; C12N 15/70; C12N 15/79; C12N 9/36; C12Q 1/68

(52) U.S. Cl. ...................... 536/23.2; 435/69.1; 435/6; 435/206; 435/252.3; 435/252.33; 435/320.1

(58) Field of Search .......................... 536/23.2; 435/6, 435/69.1, 206, 252.3, 252.33, 320.1

(56) References Cited

U.S. PATENT DOCUMENTS

| | | | |
|---|---|---|---|
| 6,083,700 A | | 7/2000 | Lal et al. ........................ 435/6 |
| 6,268,164 B1 | * | 7/2001 | Lal et al. ....................... 435/18 |
| 6,528,297 B1 | | 3/2003 | Yu et al. ...................... 435/207 |
| 6,660,485 B2 | * | 12/2003 | Lal et al. ...................... 435/7.1 |
| 2002/0111302 A1 | * | 8/2002 | Tang et al. .................... 514/12 |
| 2004/0101930 A1 | * | 5/2004 | Jackson et al. ............. 435/69.1 |

FOREIGN PATENT DOCUMENTS

| | | |
|---|---|---|
| WO | WO 2001/98353 A1 * | 12/2001 |
| WO | WO 2002/22802 A2 * | 3/2002 |
| WO | WO 2002/44340 A2 * | 6/2002 |

* cited by examiner

Primary Examiner—Ponnathapura Achutamurthy
Assistant Examiner—William W. Moore
(74) Attorney, Agent, or Firm—Merchant & Gould P.C.

(57) ABSTRACT

The present invention provided a novel human goose-type lysozyme (LYG2) and the polynucleotide encoding the LYG2. The invention also provided the corresponding expression vectors, host cells, antibodies, agonists and antagonists. The invention also provided the method for diagnosis, treatment and prevention of the diseases relative to LYG2 expression.

9 Claims, No Drawings

SEQUENCE LISTING

<160> NUMBER OF SEQ ID NOS: 4

<210> SEQ ID NO 1
<211> LENGTH: 182
<212> TYPE: PRT
<213> ORGANISM: Homo sapiens

<400> SEQUENCE: 1

Met Leu Ser Ser Val Val Phe Gly Gly Leu Ile Ala Leu Ile Gly Thr

```
                    1               5                  10                 15
                Ser Arg Ser Ser Tyr Pro Phe Ser His Ser Met Lys Pro His Leu His
                                20                  25                  30

Pro Arg Leu Tyr His Gly Cys Tyr Gly Asp Ile Met Thr Met Lys Thr
                            35                  40                  45

Ser Gly Ala Thr Cys Asp Pro Asn Ser Val Met Asn Cys Gly Ile Arg
                50                  55                  60

Gly Ser Glu Met Phe Ala Glu Met Asp Leu Arg Ala Ile Lys Pro Tyr
                65                  70                  75                  80

Gln Thr Leu Ile Lys Glu Val Gly Gln Arg His Cys Val Asp Pro Ala
                                85                  90                  95

Val Ile Ala Ala Ile Ile Ser Arg Glu Ser His Gly Gly Ser Val Leu
                                100                 105                 110

Gln Asp Gly Trp Asp His Arg Gly Leu Lys Phe Gly Leu Met Gln Leu
                                115                 120                 125

Asp Lys Gln Thr Tyr His Pro Val Gly Ala Trp Asp Ser Lys Glu His
                            130                 135                 140

Leu Ser Gln Ala Thr Gly Ile Leu Thr Glu Arg Ile Lys Ala Ile Gln
                145                 150                 155                 160

Lys Lys Phe Pro Thr Trp Ser Val Ala Gln His Leu Lys Gly Arg Leu
                                165                 170                 175

Tyr Ser Glu Tyr Phe Val
                            180

<210> SEQ ID NO 2
<211> LENGTH: 846
<212> TYPE: DNA
<213> ORGANISM: Homo sapiens
<220> FEATURE:
<221> NAME/KEY: CDS
<222> LOCATION: (114)..(662)
<223> OTHER INFORMATION:

<400> SEQUENCE: 2
gtaaaaggtt gaagtgcagt ttgctgctga gtacagaaga cctttgcaaa cagagagggg           60
agattttctc tgtaaggttg caaacaaggt cctggaagat aagattcccc gcc atg           116
                                                              Met
                                                              1 tta tcc tcc gtg gtg ttt ggg gga cta att gcc ctc att ggc act tcc           164
Leu Ser Ser Val Val Phe Gly Gly Leu Ile Ala Leu Ile Gly Thr Ser
        5                   10                  15 agg agc tca tac ccc ttc agt cac tca atg aag cct cac cta cat cca           212
Arg Ser Ser Tyr Pro Phe Ser His Ser Met Lys Pro His Leu His Pro
            20                  25                  30 cgc ctg tac cac ggc tgc tat ggg gac atc atg acc atg aag acc tct           260
Arg Leu Tyr His Gly Cys Tyr Gly Asp Ile Met Thr Met Lys Thr Ser
        35                  40                  45 ggg gcc act tgt gat cca aac agt gtg atg aac tgc ggg atc cgt ggt           308
Gly Ala Thr Cys Asp Pro Asn Ser Val Met Asn Cys Gly Ile Arg Gly
50                  55                  60                  65 tct gaa atg ttt gct gag atg gat ttg agg gcc ata aaa cct tac cag           356
Ser Glu Met Phe Ala Glu Met Asp Leu Arg Ala Ile Lys Pro Tyr Gln
                    70                  75                  80 act ctg atc aaa gaa gtc ggg cag aga cat tgc gtg gac cct gct gtc           404
Thr Leu Ile Lys Glu Val Gly Gln Arg His Cys Val Asp Pro Ala Val
                85                  90                  95 atc gca gcc atc atc tcc agg gaa agc cat ggc gga tct gtc ctg caa           452
Ile Ala Ala Ile Ile Ser Arg Glu Ser His Gly Gly Ser Val Leu Gln
            100                 105                 110
```

-continued

```
                    100                 105                 110
gac ggc tgg gac cac agg gga ctt aaa ttt ggc ttg atg cag ctt gat         500
Asp Gly Trp Asp His Arg Gly Leu Lys Phe Gly Leu Met Gln Leu Asp
    115                 120                 125 aaa caa acg tac cac cct gtc ggt gcc tgg gat agc aaa gag cac ctt         548
Lys Gln Thr Tyr His Pro Val Gly Ala Trp Asp Ser Lys Glu His Leu
130                 135                 140                 145 tca cag gct act ggg att cta aca gag aga att aag gca atc cag aaa         596
Ser Gln Ala Thr Gly Ile Leu Thr Glu Arg Ile Lys Ala Ile Gln Lys
                150                 155                 160 aaa ttc ccc acg tgg agt gtt gct cag cac ctc aaa ggt agg ctg tat         644
Lys Phe Pro Thr Trp Ser Val Ala Gln His Leu Lys Gly Arg Leu Tyr
            165                 170                 175 tct gag tac ttt gtt taa atgagcaatg aatgagacca ctgaagacca                692
Ser Glu Tyr Phe Val
            180 gtgtgacccg agactccctg ggagcatttc cacggggtca gcagtggccc tgggaggagc       752 tgtctagagg ctgcatttgc attccctgaa ccactgagtt actttgagag gtcctccatc       812 ctcaacctcc atttcctctt ctgcagaatg ttgg                                   846

<210> SEQ ID NO 3
<211> LENGTH: 23
<212> TYPE: DNA
<213> ORGANISM: Artificial
<220> FEATURE:
<221> NAME/KEY: misc_feature
<222> LOCATION: (1)..(23)
<223> OTHER INFORMATION: synthetic oligonucleotide

<400> SEQUENCE: 3
gtaaggttgc aaacaaggtc ctg                                                23

<210> SEQ ID NO 4
<211> LENGTH: 23
<212> TYPE: DNA
<213> ORGANISM: Artificial
<220> FEATURE:
<221> NAME/KEY: misc_feature
<222> LOCATION: (1)..(23)
<223> OTHER INFORMATION: synthetic oligonucleotide

<400> SEQUENCE: 4
tcacactggt cttcagtggt ctc                                                23
```

HUMAN G-TYPE LYSOZYME, THE ENCODING SEQUENCE, PREPARING METHOD AND THE USES THEREOF

FIELD OF INVENTION

This invention provides nucleic acid and amino acid sequences of a human goose-type lysozyme and the use of these sequences in the diagnosis, treatment, and prevention of autoimmune/inflammatory, renal, adrenal disorders and cancer.

BACKGROUND OF INVENTION

Lysozymes are a family of enzymes that catalyze the hydrolysis of certain mucopolysaccharides of bacterial cell walls, specifically the beta (1–4) glycosidic linkages between N-acetylmuramic acid and N-acetylglucosamine, and causes bacterial lysis. Lysozymes occur in diverse organisms including viruses, birds, and mammals. In humans, lysozymes are found in spleen, lung, kidney, leucocyte, plasma, saliva, milk, tears, and cartilage. (Online Mendelian Inheritance in Man (OMIM) #153450 Lysozyme; Weaver, L. H. et al. (1985) J. Mol. Biol. 184:739–741.)

The two known isoforms of lysozymes, chicken-type (C-type) and goose-type (G-type), were originally isolated from egg white of chicken and goose egg white, respectively. Chicken and goose-type lysozymes are similar in three-dimensional structures but different in amino acid sequences. (Nakano, T. and Graf, T. (1991) Biochim. Biophys. Acta 1090:273–276.) In chickens both isoforms of lysozyme are found in neutrophil granulocytes, but chicken-type lysozyme is found only in egg white. An analysis of the expression pattern of chicken-type and goose-type lysozyme mRNA in chicken tissues was performed. Chicken-type lysozyme mRNA is found in both adherent monocytes and macrophages and nonadherent promyelocytes and granulocytes as well as cells of the bone marrow, spleen, bursa, and oviduct. Goose-type lysozyme mRNA is found in non-adherent cells of the bone marrow and lung. The goose-type lysozyme gene cloned from chicken encodes a 211 amino acid protein containing a putative 26 amino acid N-terminal cleavable signal sequence. Homologous goose-type lysozymes are found in chicken, black swan, goose, and ostrich. Conserved residues include the three catalytic center residues Glu99, Asp112, and Asp123 (numbering from the chicken goose-type lysozyme precursor) and four cysteines that are known to form two disulfide bonds in the black swan goose-type lysozyme. Several lsozymes have been found in rabbits, including leukocytic, gastrointestinal, and possibly lymphoepithelial forms. (OMIM #153450, supra; Nakano (1991) supra; and GenBank g1310929.) A human lysozyme gene has been cloned that encodes a protein that is similar to chicken-type lysozyme. (Yoshimura, K. et al. (1988) Biochem. Biophys. Res. Commun. 150:794–801.) Lysozymes have been approved to associated with human diseases. Nakano (supra) suggested a role for lysozyme in host defense systems. Older rabbits with an inherited lysozyme deficiency show increased susceptibility to infections, especially subcutaneous abscesses. (OMIM #153450, supra.) Human lysozyme gene mutations cause hereditary systemic amyloidosis, a rare autosomal dominant disease in which amyloid deposits form in the viscera of important organs, including the kidney, adrenal glands, spleen, and liver. This disease is usually fatal by the fifth decade. The amyloid deposits contain lysozyme with amino-acid substitutions. Renal amyloidosis is the most common and potentially the most serious form of organ involvement. (Pepys, M. B. et al. 1993 Nature 362:553–557; OMIM #105200 Familial Visceral Amyloidosis; Cotran, R. S. et al. 1994 Robbins Pathologic Basis of Disease, W.B. Saunders Company, Philadelphia, Pa., pp. 231–238.) Goose-type lysozyme is expressed in avian promyelocytes transformed with avian myeloblastosis virus containing the L106 mutant form of the v-myb oncogene. (Nakano, T. and Graf. T. (1992) Oncogene 7:527–534; and Nakano 1991 supra.)

Therefore, it is a long need in the art to develop new lysozyme.

SUMMARY OF INVENTION

The invention provides a polynucleotide sequence named human LYG2, which encoding human goose-type lysozyme 2. (The published human goose-type lysozyme is named LYG1 in this application.)

The invention also provides a new human goose-type lysozyme 2.

The invention further provides the new human goose-type lysozyme 2 (LYG2), the polynucleotides encoding LYG2, and the use of these compositions for the diagnosis, treatment, or prevention of autoimmune/inflammatory, renal, and adrenal disorders and cancer.

The invention further provides a substantially purified variant having at least 90% amino acid sequence identity to the amino acid sequence of SEQ ID NO: 1 or a fragment of SEQ ID NO: 1. The invention also provides an isolated and purified polynucleotide encoding the polypeptide comprising the sequence of SEQ ID NO: 1 or a fragment of SEQ ID NO: 1. The invention also includes an isolated and purified polynucleotide variant having at least 70% polynucleotide sequence identity to the polynucleotide encoding the polypeptide comprising the amino acid sequence of SEQ ID NO: 1 or a fragment of SEQ ID NO: 1.

The invention further provides an isolated and purified polynucleotide which hybridizes under stringent conditions to the polynucleotide encoding the polypeptide comprising the amino acid sequence of SEQ ID NO: 1 or a fragment of SEQ ID NO: 1, as well as an isolated and purified polynucleotide which is complementary to the polynucleotide encoding the polypeptide comprising the amino acid sequence of SEQ ID NO: 1 or a fragment of SEQ ID NO: 1.

The invention also provides an isolated and purified polynucleotide comprising the polynucleotide sequence of 1–846 or 114–662 in SEQ ID NO: 2 or a fragment thereof, and an isolated and purified polynucleotide variant having at least 70% polynucleotide sequence identity to the polynucleotide comprising the polynucleotide sequence of SEQ ID NO: 2 or a fragment of SEQ ID NO: 2. The invention also provides an isolated and purified polynucleotide having a sequence complementary to the polynucleotide comprising the polynucleotide sequence of SEQ ID NO: 2 or a fragment of SEQ ID NO: 2.

The invention further provides an expression vector comprising at least a fragment of the polynucleotide encoding the polypeptide comprising the sequence of SEQ ID NO: 1 or a fragment of SEQ ID NO: 1. In another aspect, the expression vector is contained within a host cell.

The invention also provides a method for producing a polypeptide comprising the amino acid sequence of SEQ ID NO: 1 or a fragment of SEQ ID NO: 1, the method comprising the steps of: (a) culturing the host cell comprising an expression vector containing at least a fragment of a polynucleotide encoding the polypeptide comprising the amino acid sequence of SEQ ID NO: 1 or a fragment of SEQ ID NO: 1 under conditions suitable for the expression of the polypeptide; and (b) recovering the polypeptide from the host cell culture.

The invention also provides a pharmaceutical composition comprising a substantially purified polypeptide having the sequence of SEQ ID NO: 1 or a fragment of SEQ ID NO: 1 in conjunction with a suitable pharmaceutical carrier.

The invention further includes a purified antibody which binds to a polypeptide comprising the sequence of SEQ ID NO: 1 or a fragment of SEQ ID NO: 1, as well as a purified agonist and a purified antagonist of the polypeptide.

The invention also provides a method for treating or preventing an autoimmune/inflammatory disorder, the method comprising administering to a subject in need of such treatment an effective amount of a pharmaceutical composition comprising substantially purified polypeptide having the amino acid sequence of SEQ ID NO: 1 or a fragment of SEQ ID NO: 1.

The invention also provides a method for treating or preventing a renal disorder, the method comprising administering to a subject in need of such treatment an effective amount of a pharmaceutical composition comprising substantially purified polypeptide having the amino acid sequence of SEQ ID NO: 1 or a fragment of SEQ ID NO: 1.

The invention also provides a method for treating or preventing an adrenal disorder, the method comprising administering to a subject in need of such treatment an effective amount of a pharmaceutical composition comprising substantially purified polypeptide having the amino acid sequence of SEQ ID NO: 1 or a fragment of SEQ ID NO: 1.

The invention also provides a method for treating or preventing a cancer, the method comprising administering to a subject in need of such treatment an effective amount of an antagonist of the polypeptide having the amino acid sequence of SEQ ID NO: 1 or a fragment of SEQ ID NO: 1.

The invention also provides a method for detecting a polynucleotide encoding a polypeptide comprising the amino acid sequence of SEQ ID NO: 1 or a fragment of SEQ ID NO: 1 in a biological sample containing nucleic acids, the method comprising the steps of: (a) hybridizing the polynucleotide encoding the polypeptide comprising the amino acid sequence of SEQ ID NO: 1 or a fragment of SEQ ID NO: 1 to at least one of the nucleic acids of the biological sample, thereby forming a hybridization complex; and (b) detecting the hybridization complex, wherein the presence of the hybridization complex correlates with the presence of a polynucleotide encoding the polypeptide comprising the amino acid sequence of SEQ ID NO: 1 or a fragment of SEQ ID NO: 1 in the biological sample. In one aspect, this method further comprises amplifying the polynucleotide prior to the hybridizing step.

DEFINITIONS

"LYG2" refers to the amino acid sequences, or variant thereof, of substantially purified LYG2 obtained from any species, particularly a mammalian species, including bovine, ovine, porcine, murine, equine, and preferably the human species, from any source, whether natural, synthetic, semi-synthetic, or recombinant.

The term "agonist" refers to a molecule which, when bound to LYG2, increases or prolongs the duration of the effect of LYG2. Agonists may include proteins, nucleic acids, carbohydrates, or any other molecules which bind to and modulate the effect of LYG2.

An "allelic variant" is an alternative form of the gene encoding LYG2. Allelic variants may result from at least one mutation in the nucleic acid sequence and may result in altered mRNAs or in polypeptides whose structure or function may or may not be altered. Any given natural or recombinant gene may have none, one, or many allelic forms "Altered" nucleic acid sequences encoding LYG2 include those sequences with deletions, insertions, or substitutions of different nucleotides, resulting in a polynucleotide the same as LYG2 or a polypeptide with at least one functional characteristic of LYG2. Included within this definition are polymorphisms which may or may not be readily detectable using a particular oligonucleotide probe of the polynucleotide encoding LYG2, and improper or unexpected hybridization to allelic variants, with a locus other than the normal chromosomal locus for the polynucleotide sequence encoding LYG2. The encoded protein may also be "altered," and may contain deletions, insertions, or substitutions of amino acid residues which produce a silent change and result in a functionally equivalent LYG2. Deliberate amino acid substitutions may be made on the basis of similarity in polarity, charge, solubility, hydrophobicity, hydrophilicity, and/or the amphipathic nature of the residues, as long as the biological or immunological activity of LYG2 is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of LYG2 which are preferably at least 5 to about 15 amino acids in length, most preferably at least 14 amino acids, and which retain some biological activity or immunological activity of LYG2. Where "amino acid sequence" refers to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to LYG2, decreases the amount or the duration of the effect of the biological or immunological activity of LYG2. Antagonists may include proteins, nucleic acids, carbohydrates, antibodies, or any other molecules which decrease the effect of LYG2.

The term "antibody" refers to intact molecules as well as to fragments thereof, such as Fab, F(ab')$_2$, and Fv fragments, which are capable of binding the epitopic determinant. Antibodies that bind LYG2 polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "biologically active," refers to a protein having structural, regulatory, or biochemical functions of a naturally occurring molecule. Likewise, "immunologically active" refers to the capability of the natural, recombinant, or synthetic LYG2, or of any oligopeptide thereof, to induce a specific immune response in appropriate animals or cells and to bind with specific antibodies.

The terms "complementary" or "complementarity" refer to the natural binding of polynucleotides by base pairing. For example, the sequence "5' A-G-T 3'" binds to the complementary sequence "3'T-C-A 5'" Complementarity between two single-stranded molecules may be "partial," such that only some of the nucleic acids bind, or it may be "complete," such that total complementarity exists between the single stranded molecules "Consensus sequence" refers to a nucleic acid sequence which has been resequenced to resolve uncalled bases, or which has been assembled from the overlapping sequences. Some sequences have been both extended and assembled to produce the consensus sequence.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the PCGENE program. The PCGENE program can create alignments between two or more sequences according to different methods, e.g., the clustal method. The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid bonds with a complementary strand through base pairing.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides arrayed on a substrate, e.g., paper, nylon or any other type of membrane, filter, chip, glass slide, or any other suitable solid support. The term "element" or "microarray element" refers to the polynucleotides for hybridization on the surface of substrate.

The term "modulate" refers to a change in the activity of LYG2. For example, modulation may cause an increase or a decrease in protein activity, binding characteristics, or any other biological, functional, or immunological properties of LYG2.

The phrases "nucleic acid" or "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray.

The term "oligonucleotide" is substantially equivalent to the terms "amplimer," "primer," "oligomer," and "probe," as these terms are commonly defined in the art.

"Peptide nucleic acid" (PNA) refers to an antisense molecule or anti-gene agent, which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation. (See, e.g., Nielsen, P. E. et al. (1993) Anticancer Drug Des. 8:53–63.)

The term "sample" is used in its broadest sense. A biological sample suspected of containing nucleic acids encoding LYG2, or fragments thereof, or LYG2 itself, may comprise a body fluid; an extract from a cell, chromosome, organelle, or membrane isolated from a cell; a cell; genomic DNA, RNA, or cDNA, in solution or bound to a solid support; a tissue; a tissue print; etc.

The terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions that permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of LYG2 polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both.

The term "variant," when used in the context of a polynucleotide sequence, may encompasses a polynucleotide sequence related to LYG2. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention.

The invention is based on the discovery of a new human goose-type lysozyme 2 (LYG2), the polynucleotides encoding LYG2, and the use of these compositions for the diagnosis, treatment, or prevention of autoimmune/inflammatory, renal, and adrenal disorders and cancer.

In one embodiment, the invention encompasses a polypeptide comprising the amino acid sequence of SEQ ID NO: 1. LYG2 is 182 amino acids in length and four potential protein kinase C phosphorylation sites at residues T16, S26, T45, and T152. LYG2 has a potential signal sequence from residue M1 through about residue S19. Analysis indicates that LYG2 has sequence homology with the lysozyme G signature from residues S4 through T174. LYG has chemical and structural similarity with human goose-type lysozyme. In particular, LYG2 and human goose-type lysozyme1(LYG1) share 31.2% identity. LYG2 and human goose-type lysozyme share the four cysteines conserved in goose-type lysozymes that are proposed to form disulfide bonds at residues C29, C53, C62, and C92 of LYG2. LYG2 contains the conserved goose-type lysozyme catalytic center aspartic acid residue at D105 and has a charged residue E105 and an acidic residue Q127, at the other two catalytic center residue sites.

The invention also encompasses LYG2 variants. A preferred LYG2 variant is one which has at east about 80%, more preferably at least about 90%, and most preferably at least about 95% amino acid sequence identity to the LYG2 amino acid sequence, and which contains at least one functional or structural characteristic of LYG2.

The invention also encompasses polynucleotides that encode LYG2. In a particular embodiment, the invention encompasses a polynucleotide sequence comprising the sequence of SEQ ID NO: 2, which encodes an LYG2.

The invention also encompasses a variant of a polynucleotide sequence encoding LYG2. In particular, such a variant polynucleotide sequence will have at least about 70%, more preferably at least about 85%, and most preferably at least about 95% polynucleotide sequence identity to the polynucleotide sequence encoding LYG2. A particular aspect of the invention encompasses a variant of SEQ ID NO: 2 which has at least about 70%, more preferably at least about 85%, and most preferably at least about 95% polynucleotide sequence identity to SEQ ID NO: 2. Any one of the polynucleotide variants described above can encode an amino acid sequence which contains at least one functional or structural characteristic of LYG2.

It will be appreciated by those skilled in the art that as a result of the degeneracy of the genetic code, a multitude of polynucleotide sequences encoding LYG2, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring LYG2.

It may be advantageous to produce nucleotide sequences encoding LYG2 possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding LYG2 and its derivatives without altering the encoded amino acid sequences include the production of RNA transcripts having more desirable properties, such as a greater half-life, than transcripts produced from the naturally occurring sequence.

The invention also encompasses production of DNA sequences that encode LYG2 and LYG2 derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding LYG2 or any fragment thereof.

The washing steps, which follow hybridization, can also vary in stringency. Wash stringency conditions can be defined by salt concentration and by temperature. As above, increasing temperature can increase by decreasing salt concentration or wash stringency. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing and analysis are well known in the art. The methods may employ such enzymes as the Klenow fragment of DNA polymerase I, Taq DNA polymerase or combinations of polymerases and proofreading exonucleases. Preferably, sequence preparation is automated with machines, e.g., the ABI 377 systems (PE Biosystems). Sequences can be analyzed using computer programs and algorithms well known in the art (such as PCGENE, Clustal.)

The nucleic acid sequences encoding LYG2 may be extended utilizing a partial nucleotide sequence and employing various PCR-based methods known in the art to detect upstream sequences, such as promoters and regulatory elements. For example, one method, which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods that may be used to retrieve unknown sequences are known in the art. (See, e.g., Parker, J. D. et al. (1991) Nucleic Acids Res. 19:3055–3060). Additionally, one may use PCR and nested primers to walk genomic DNA. This procedure avoids the need to screen libraries and is useful in finding intron/exon junctions. For all PCR-based methods, primers may be designed using commercially available software, such as OLIGO 4.06 Primer Analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems, which are commercially available, may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR analysis software (PE Biosystems)), and the entire process from loading of samples to computer analysis and electronic data display may be computer controlled. Capillary electrophoresis is especially preferable for sequencing small DNA fragments, which may be present in limited amounts in a particular sample.

In another embodiment of the invention, polynucleotide sequences or fragments thereof, which encode LYG2, may be cloned in recombinant DNA molecules that direct expression of LYG2, or fragments or functional equivalents thereof, in appropriate host cells. Due to the inherent degeneracy of the genetic code, other DNA sequences, which encode substantially the same, or a functionally equivalent amino acid sequence may be produced and used to express LYG2.

In another embodiment, sequences encoding LYG2 may be synthesized, in whole or in part, using chemical methods well known in the art. (See, e.g., Caruthers, M. H. et al. (1980) Nucl. Acids Symp. Ser(2) 215–223, and Horn, T. et al. (1980) Nucl. Acids Res. Symp. Ser. 225–232.) Alternatively, LYG2 itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI model 43/A peptide synthesizer (PE Biosystems). Additionally, the amino acid sequence of LYG2, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) Proteins, Structures and Molecular Properties, WH Freeman and Co., New York, N.Y.)

In order to express a biologically active LYG2, the nucleotide sequences encoding LYG2 or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding LYG2. Such elements may vary in their strength and specificity. Specific initiation signals may also be used to achieve more efficient translation of sequences encoding LYG2. Such signals include the ATG initiation codon and adjacent sequences, e.g. the Kozak sequence. In cases where sequences encoding LYG2 and its initiation codon and upstream regulatory sequences are inserted into the appropriate expression vector, no additional transcriptional or translational control signals may be needed. However, in cases where only coding sequence, or a fragment thereof, is inserted, the vector should provide exogenous translational control signals including an in-frame ATG initiation codon. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding LYG2 and appropriate transcriptional and translational control elements. These methods include in vitro recombinant DNA techniques, synthetic techniques, and in vivo genetic recombination. (See, e.g., Sambrook, J. et al. (1989) Molecular Cloning, A Laboratory Manual, Cold Spring Harbor Press, Plainview, N.Y., ch. 4, 8, and 16–17; and Ausubel, F. M. et al. (1995, and periodic supplements) Current Protocols in Molecular Biology, John Wiley & Sons, New York, N.Y., ch. 9, 13, and 16.)

A variety of expression vector/host systems may be utilized to contain and express sequences encoding LYG2. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The host cell employed does not limit the invention.

In bacterial systems, a number of cloning and expression vectors may be selected depending upon the use intended for polynucleotide sequences encoding LYG2. For example, routine cloning, subcloning, and propagation of polynucleotide sequences encoding LYG2 can be achieved using a multifunctional *E. coli* vector such as PBLUESCRIPT phagemid (Stratagene) or PSPORT2 plasmid (Life Technologies). Ligation of sequences encoding LYG2 into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of LYG2 are needed, e.g. for the production of antibodies, vectors which direct high level expression of LYG2 may be used. For example, vectors containing the strong, inducible T5 or T7 bacteriophage promoter may be used.

Yeast expression systems may be used for production of LYG2. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of LYG2. Transcription of sequences encoding LYG2 may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in McGraw Hill Yearbook of Science and Technology (1992) McGraw Hill, New York, N.Y.; pp. 191–196.)

In mammalian cells, a number of viral-based expression systems may be utilized. In cases where an adenovirus is used as an expression vector, sequences encoding LYG2 may be ligated into an adenovirus transcription/translation complex consisting of the late promoter and tripartite leader sequence. Insertion in a non-essential E1 or E3 region of the viral genome may be used to obtain infective virus which expresses LYG2 in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345–355.)

For long-term production of recombinant proteins in mammalian systems, stable expression of LYG2 in cell lines is preferred. For example, sequences encoding LYG2 can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Although the presence/absence of marker gene expression suggests that the gene of interest is also present, the presence and expression of the gene may need to be confirmed. For example, if the sequence encoding LYG2 is inserted within a marker gene sequence, transformed cells containing sequences encoding LYG2 can be identified by the absence of marker gene function. Alternatively, a marker gene can be placed in tandem with a sequence encoding LYG2 under the control of a single promoter. Expression of the marker gene in response to induction or selection usually indicates expression of the tandem gene as well.

In general, host cells that contain the nucleic acid sequence encoding LYG2 and that express LYG2 may be identified by a variety of procedures known to those of skill in the art. These procedures include, but are not limited to, DNA—DNA or DNA—RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of LYG2 using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on LYG2 is preferred, but a competitive binding assay may be employed. These and other assays are well known in the art. (See, e.g., Hampton, R. et al. (1990) Serological Methods, a Laboratory Manual, APS Press, St Paul, Minn., Section IV; Coligan, J. E. et al. (1997 and periodic supplements) Current Protocols in Immunology, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding LYG2 include oligolabeling, nick translation, end-labeling, or PCR amplification using a labeled nucleotide. Alternatively, the sequences encoding LYG2, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech and Promega (Madison, Wis.). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding LYG2 may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode LYG2 may be designed to contain signal sequences which direct secretion of LYG2 through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Different host cells, which have specific cellular machinery and characteristic mechanisms for post-translational activities are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding LYG2 may be ligated to a heterologous sequence resulting in translation of a fusion protein in any of the aforementioned host systems. For example, a chimeric LYG2 protein containing a heterologous moiety that can be recognized by a commercially available antibody may facilitate the screening of peptide libraries for inhibitors of LYG2 activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the LYG2 encoding sequence and the heterologous protein sequence, so that LYG2 may be cleaved away from the heterologous moiety following purification.

In a further embodiment of the invention, synthesis of radiolabeled LYG2 may be achieved in vitro. These systems couple transcription and translation of protein-coding sequences operably associated with the T7, T3, or SP6 promoters. Translation takes place in the presence of a radiolabeled amino acid precursor, preferably $^{35}$S-methionine.

Fragments of LYG2 may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the ABI model 43/A peptide synthesizer (PE Biosystems). Various fragments of LYG2 may be synthesized separately and then combined to produce the full length molecule.

Chemical and structural similarity, e.g., in the context of sequences and motifs, exists between LYG2 and LYG1. In addition, LYG2 is expressed in cancerous, inflamed, kidney, breast, adrenal gland, colon, and nervous tissues. Therefore, LYG2 appears to play a role in autoimmune/inflammatory, renal, and adrenal disorders and cancer.

Therefore, in one embodiment, LYG2 or a fragment or derivative thereof may be administered to a subject to treat or prevent an autoimmune/inflammatory disorder. Such autoimmune/inflammatory disorders can include, but are not limited to, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

In another embodiment, a vector capable of expressing LYG2 or a fragment or derivative thereof may be administered to a subject to treat or prevent an autoimmune/inflammatory disorder including, but not limited to, those described above.

In a further embodiment, a pharmaceutical composition comprising a substantially purified LYG2 in conjunction with a suitable pharmaceutical carrier may be administered to a subject to treat or prevent an autoimmune/inflammatory disorder including, but not limited to, those provided above.

In still another embodiment, an agonist which modulates the activity of LYG2 may be administered to a subject to treat or prevent an autoimmune/inflammatory disorder including, but not limited to, those listed above.

Therefore, in another embodiment, LYG2 or a fragment or derivative thereof may be administered to a subject to treat or prevent a renal disorder. Such renal disorders can include, but are not limited to, renal amyloidosis, hypertension; primary aldosteronism; Addison's disease; renal failure; glomerulonephritis; chronic glomerulonephritis; tubulointerstitial nephritis; cystic disorders of the kidney and dysplastic malformations such as polycystic disease, renal dysplasias, and cortical or medullary cysts; inherited polycystic renal diseases (PRD) such as recessive and autosomal dominant PRD; medullary cystic disease; medullary sponge kidney and tubular dysplasia; Alport's syndrome; non-renal cancers which affect renal physiology, such as bronchogenic tumors of the lungs or tumors of the basal region of the brain; multiple myeloma; adenocarcinomas of the kidney;

metastatic renal carcinoma; nephrotoxic disorders produced by the ingestion, injection, inhalation, or absorption of any pharmaceutical, chemical, or biological agent such as heavy metals, all classes of antibiotics, analgesics, solvents, oxalosis-inducing agents, anticancer drugs, herbicides and pesticides, botanicals and biologicals, and antiepileptics.

In another embodiment, a vector capable of expressing LYG2 or a fragment or derivative thereof may be administered to a subject to treat or prevent a renal disorder including, but not limited to, those described above.

In a further embodiment, a pharmaceutical composition comprising a substantially purified LYG2 in conjunction with a suitable pharmaceutical carrier may be administered to a subject to treat or prevent a renal disorder including, but not limited to, those provided above.

In still another embodiment, an agonist which modulates the activity of LYG2 may be administered to a subject to treat or prevent a renal disorder including, but not limited to, those listed above.

Therefore, another embodiment, LYG2 or a fragment or derivative thereof may be administered to a subject to treat or prevent an adrenal disorder. Such adrenal disorders can include, but are not limited to, hyperplasia, carcinoma, or adenoma of the adrenal cortex, hypertension associated with alkalosis, amyloidosis, hypokalemia, Cushing's disease, Liddle's syndrome, and Arnold-Healy-Gordon syndrome, pheochromocytoma tumors, and Addison's disease.

In another embodiment, a vector capable of expressing LYG2 or a fragment or derivative thereof may be administered to a subject to treat or prevent an adrenal disorder including, but not limited to, those described above.

In a further embodiment, a pharmaceutical composition comprising a substantially purified LYG2 in conjunction with a suitable pharmaceutical carrier may be administered to a subject to treat or prevent an adrenal disorder including, but not limited to, those provided above.

In still another embodiment, an agonist which modulates the activity of LYG2 may be administered to a subject to treat or prevent an adrenal disorder including, but not limited to, those listed above.

In a further embodiment, an antagonist of LYG2 may be administered to a subject to treat or prevent a cancer. Such a cancer may include, but is not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds LYG2 may be used directly as an antagonist or indirectly as a targeting or delivery mechanism for bringing a pharmaceutical agent to cells or tissue which express LYG2.

In an additional embodiment, a vector expressing the complement of the polynucleotide encoding LYG2 may be administered to a subject to treat or prevent a cancer including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of LYG2 may be produced using methods which are generally known in the art. In particular, purified LYG2 may be used to produce antibodies or to screen libraries of pharmaceutical agents to identify those which specifically bind LYG2. Antibodies to LYG2 may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of polyclonal antibodies, various hosts including goats, rabbits, rats, mice, humans, and others may be immunized by injection with LYG2 or with any fragment or oligopeptide thereof which has immunogenic properties. Rats and mice are preferred hosts for downstream applications involving monoclonal antibody production. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable. (For review of methods for antibody production and analysis, see, e.g., Harlow, E. and Lane, D. (1988) Antibodies: A Laboratory Manual, Cold Spring Harbor Laboratory, Cold Spring Harbor, N.Y.)

It is preferred that the oligopeptides, peptides, or fragments used to induce antibodies to LYG2 have an amino acid sequence consisting of at least about 5 amino acids, and, more preferably, of at least about 14 amino acids. It is also preferable that these oligopeptides, peptides, or fragments are identical to a portion of the amino acid sequence of the natural protein and contain the entire amino acid sequence of a small, naturally occurring molecule. Short stretches of LYG2 amino acids may be fused with those of another protein, such as KLH, and antibodies to the chimeric molecule may be produced.

Monoclonal antibodies to LYG2 may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art; to produce LYG2-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody. fragments which contain specific binding sites for LYG2 may also be generated. For example, such fragments include, but are not limited to, F(ab')$_2$ fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. 1989, Science 246:1275–1281.)

Various immunoassays may be used for screening to identify antibodies having the desired specificity and minimal cross-reactivity. Numerous protocols for competitive binding or immunoradiometric assays using either polyclonal or monoclonal antibodies with established specificities are well known in the art. Such immunoassays typically involve the measurement of complex formation between LYG2 and its specific antibody. A two-site, monoclonal-based immunoassay utilizing monoclonal antibodies reactive to two non-interfering LYG2 epitopes is preferred, but a competitive binding assay may also be employed.

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is preferred for use in procedures requiring precipitation of LYG2-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding LYG2, or any fragment or complement thereof, may be used for therapeutic purposes. In one aspect, the complement of the polynucleotide encoding LYG2 may be used in situations in which it would be desirable to block the transcription of the mRNA. In particular, cells may be transformed with sequences complementary to polynucleotides encoding LYG2. Thus, complementary molecules or fragments may be used to modulate LYG2 activity, or to achieve regulation of gene function. Such technology is now well known in the art, and sense or antisense oligonucleotides or larger fragments can be designed from various locations along the coding or control regions of sequences encoding LYG2.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding LYG2. (See, e.g., Sambrook, supra; and Ausubel, supra.)

Genes encoding LYG2 can be turned off by transforming a cell or tissue with expression vectors which express high levels of a polynucleotide, or fragment thereof, encoding LYG2. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding LYG2. Oligonucleotides derived from the transcription initiation site, e.g., between about positions –10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, Molecular and Immunologic Aproaches, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding LYG2. Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding LYG2. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient.

Delivery by transfection, by liposome injections, or by polycationic amino polymers may be achieved using methods which are well known in the art. (See, e.g., Goldman, C. K. et al. (1997) Nature Biotechnology 15:462–466.) Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of LYG2, antibodies to LYG2, and mimetics, agonists, antagonists, or inhibitors of LYG2. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, subcutaneous or intraperitoneal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for injunction may be formulated in aqueous solutions, preferably in physiologically compatible buffers such as Hanks' solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

In another embodiment, antibodies which specifically bind LYG2 may be used for the diagnosis of disorders characterized by expression of LYG2, or in assays to monitor patients being treated with LYG2 or agonists, antagonists, or inhibitors of LYG2. Antibodies useful for diagnostic purposes may be prepared in the same manner as described above for therapeutics. Diagnostic assays for LYG2 include methods which utilize the antibody and a label to detect LYG2 in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring LYG2, including ELISAs, RIAs, and FACS, are known in the art and provide a basis for diagnosing altered or abnormal levels of LYG2 expression. Normal or standard values for LYG2 expression are established by combining body fluids or cell extracts taken from normal mammalian subjects, preferably human, with antibody to LYG2 under conditions suitable for complex formation. The amount of standard complex formation may be quantitated by various methods, preferably by photometric means. Quantities of LYG2 expressed in subject, control, and disease samples from biopsied tissues are compared with the standard values. Deviation between standard and subject values establishes the parameters for diagnosing disease.

In another embodiment of the invention, the polynucleotides encoding LYG2 may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of LYG2 may be correlated with disease. The diagnostic assay may be used to determine absence, presence, and excess expression of LYG2, and to monitor regulation of LYG2 levels during therapeutic intervention.

A probe comprising the contiguous nucleotide sequence of nucleotides 10 through 846 of SEQ ID NO: 2 or the complement thereof. Probes may also be used for the detection of related sequences, and should preferably have at least 50% sequence identity to any of the LYG2 encoding sequences. The hybridization probes of the subject invention may be DNA or RNA.

Means for producing specific hybridization probes for DNAs encoding LYG2 include the cloning of polynucleotide sequences encoding LYG2 or LYG2 derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding LYG2 may be used for the diagnosis of a disorder associated with expression of LYG2. Examples of such a disorder include, but are not limited to, autoimmune/inflammatory disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; renal disorders such as renal amyloidosis, hypertension; primary aldosteronism; Addison's disease; renal failure; glomerulonephritis; chronic glomerulonephritis; tubulointerstitial nephritis; cystic disorders of the kidney and dysplastic malformations such as polycystic disease, renal dysplasias, and cortical or medullary cysts; inherited polycystic renal diseases (PRD) such as recessive and autosomal dominant PRD; medullary cystic disease; medullary sponge kidney and tubular dysplasia; Alport's syndrome; non-renal cancers which affect renal physiology, such as bronchogenic tumors of the lungs or tumors of the basal region of the brain; multiple myeloma; adenocarcinomas of the kidney; metastatic renal carcinoma; nephrotoxic disorders produced by the ingestion, injection, inhalation, or absorption of any pharmaceutical, chemical, or biological agent such as heavy metals, all classes of antibiotics, analgesics, solvents, oxalosis-inducing agents, anticancer drugs, herbicides and pesticides, botanicals and biologicals, and antiepileptics; adrenal disorders such as hyperplasia, carcinoma, or adenoma of the adrenal cortex, hypertension associated with alkalosis, amyloidosis, hypokalemia, Cushing's disease, Liddle's syndrome, and Arnold-Healy-Gordon syndrome, pheochromocytoma tumors, and Addison's disease; and cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The polynucleotide sequences encoding LYG2 may be used in Southern or Northern analysis, dot blot, or other membrane-based technologies; in PCR technologies; in dipstick, pin, and ELISA-like assays; and in microarrays utilizing fluids or tissues from patients to detect altered LYG2 expression. Such qualitative or quantitative methods are well known in the art.

The nucleotide sequences encoding LYG2 may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding LYG2 in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of LYG2, a normal or standard profile for expression is established. This may be accomplished by combining body fluids or cell extracts taken from normal subjects, either animal or human, with a sequence, or a fragment thereof, encoding LYG2, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

Additional diagnostic uses for oligonucleotides designed from the sequences encoding LYG2 may involve the use of PCR. These oligomers may be chemically synthesized, generated enzymatically, or produced in vitro. Oligomers will preferably contain a fragment of a polynucleotide encoding LYG2, or a fragment of a polynucleotide complementary to the polynucleotide encoding LYG2, and will be employed under optimized conditions for identification of a specific gene or condition. Oligomers may also be employed under less stringent conditions for detection or quantitation of closely related DNA or RNA sequences.

Methods which may also be used to quantitate the expression of LYG2 include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 212:229–236.) The speed of quantitation of multiple samples may be accelerated by running the assay in an ELISA-like format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding LYG2 may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial PI constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) Molecular Biology and Biotechnology, VCH Publishers New York, N.Y., pp. 965–968.) Examples of genetic map data can be found in various scientific journals or at the Online Mendelian Inheritance in Man (OMIM) site. Correlation between the location of the gene encoding LYG2 on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, LYG2, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between LYG2 and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with LYG2, or fragments thereof, and washed. Bound LYG2 is then detected by methods well known in the art. Purified LYG2 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding LYG2 specifically compete with a test compound for binding LYG2. In this manner, antibodies can be used to detect the presence of any peptide which shares one or more antigenic determinants with LYG2.

In additional embodiments, the nucleotide sequences which encode LYG2 may be used in any molecular biology techniques that have yet to be developed, provided the new techniques rely on properties of nucleotide sequences that are currently known, including, but not limited to, such properties as the triplet genetic code and specific base pair interactions.

The full length human LYG2 nucleotide sequence or its fragment of the invention can be prepared by PCR amplification, recombinant method and synthetic method. For PCR amplification, one can obtain said sequences by designing primers based on the nucleotide sequence disclosed in the invention, especially the sequence of ORF, and using cDNA library commercially available or prepared by routine techniques known in the art as a template. When the sequence is long, it is usually necessary to perform two or more PCR amplifications and link the amplified fragments together in the correct order.

Once the sequence is obtained, a great amount of the sequences can be produced by recombinant methods.

Usually, said sequence is cloned in a vector which is transformed into a host cell. Then the sequence is isolated from the amplified host cells using conventional techniques.

Further, the sequence can be produced by synthesis, especially when the sequence is short. Typically, several small fragments are synthesized and linked together to obtain a long sequence.

At present, it is completely feasible to chemically synthesize the DNA sequence encoding the protein of the invention, or the fragments or derivatives thereof and then introduce the DNA sequence into DNA molecules (such as vectors) and cells. In addition, the mutation can be introduced into the sequence of the protein by chemical synthesis.

In another aspect, since LYG2 is derived from human, it is predicted to have more activity and/or less side effects (e.g., less or no immunogenicity) than the proteins of same family from other species when administrated to human.

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al., in Molecule Clone; A Laboratory Manual, New York: Cold Spring Harbor Laboratory Press, 1989, or as instructed by the manufacturers, unless otherwise specified.

EXAMPLE 1

The Cloning and Sequencing of LYG2 cDNA Sequence

1. Search the Human EST Database

The homologous ESTs were obtained by searching the GenBank human EST database, using LYG1 cDNA sequence as probes. Search the EST database again using the said EST to extend sequences, which were partly overlapped with sequences of the probes. Align the sequences above to get a new extended sequence and then search the database once more to extend the sequence more. Repeat the extension steps again and again until the sequences could not be extended any more.

2. Amplification with Primers

Primers were designed according to the EST sequences obtained after extension. PCR with forward primers A1: 5'-GTAAGGTTGCAAACAAGGTCCTG (SED ID NO.3) and reverse primer B1: 5'-TCACACTGGTCTTCAGTGGTCTC (SED ID NO.4) was carried out using human testis λ gt10 cDNA library (Clontech) as template. The PCR condition was 4 mins at 93° C.; followed by 35 cycles with 1 min at 93° C., 1 min at 70° C., and 1 min at 72° C.; and, finally, 5 mins at 72° C. The PCR fragments were detected by electrophoresis. The target fragment was 846 bp.

3. Sequencing the PCR Products

The obtained PCR product was linked with pGEM-T® vector (Promega) and transformed into *E. coli* JM103. The plasmids were then extracted using QIAprep Plasmid Kit (QIAGEN). The oriented serial deletion of the inserted fragments was carried out with Doubles-Stranded Nested Deletion Kit (Pharmacia), and the deletants were quickly identified by PCR and arranged in order. The deletants successively cut-off were sequenced with SequiTherm EXCEL™ DNA Sequencing Kit (Epicentre Technologies). A full length cDNA sequence of 846 bp was obtained by over lapping the sequences with computer software. The detailed sequence is shown in SEQ IN NO: 2 with an open reading frame located at nucleotides 114–662.

The amino acid sequence of human LYG2 deduced from full length cDNA sequence comprises 182 amino acids as shown in SEQ ID No. 1.

EXAMPLE 2

Homologous Comparison

The full length cDNA sequence of LYG2 and the coded protein were used for homologous screening Non-redundant GenBank+EMBL+DDBJ+PDB and GenBank CDS translations+PDB+SwissProt+Spupdate+PIR databases by BLAST algorithm. Analogous computer techniques applying BLAST were used to search for identical or related molecules in nucleotide databases such as GenBank database. This analysis is much faster than multiple membrane-based hybridizations. In addition, the sensitivity of the computer search can be modified. The result showed that they shared high homology to other members of the goose-lysozyme family. The nucleotic acid sequence and amino acid sequence shares about 46% and 31% identity with those of LYG1. Additionally, the amino acid sequence of LYG2 shared 39%, 40% and 36% with goose-type lysozyme from blackswan (sp|P00717) ostrich (sp|P00718) and chicken (sp|P00719), indicating LYG2 belongs to goose-type lysozyme gene family and has the same or similar functions.

EXAMPLE 3

Northern Analysis

Northern analysis is a technique to examine the transcription of genes, which includes hybridizing the labeled nucleotide acid sequence to the membrane containing RNA isolated from specific cells or tissues.

Northern analysis showed LYG2 was expressed in all the tissues but the expressions were quite low except for a high expression in brain and testis.

EXAMPLE 4

Labeling and Use of Individual Hybridization Probes

Hybridization probes derived from SEQ ID NO: 2 are employed to screen cDNAs, genomic DNAs, or mRNAs. Although the labeling of oligonucleotides, consisting of 23 base pairs, is specifically described, essentially the same procedure is used with larger nucleotide fragments. Oligonucleotides are designed using software such as PGENE software and labeled by combining 50 pmol of each oligomer, 250 $\mu$Ci of $\gamma$-$^{32}$P adenosine triphosphate, and T4 polynucleotide kinase. The labeled oligonucleotides are substantially purified using a SEPHADEX G-25 superfine size exclusion dextran bead column (Amersham Pharmacia Biotech). The purified probe was immobilized on the hybridization membrane. The membrane was washed to reduce the background noise to 7–10 cpm and was ready for use.

The human genomic DNA was digested with one of the following endonucleases: Ase I, Bgl II, Eco RI, Pst I, Xbal, or Pvu II (NEN Life Science Products). The DNA from each digest is fractionated on a 0.7% agarose gel and transferred to nylon membranes. Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Eastman Kodak, Rochester, N.Y.) is exposed to the blots to film for several hours, hybridization patterns were compared visually.

EXAMPLE 5

Microarrays

Microarrays also names DNA chips. A chemical coupling procedure and an ink jet device can be used to synthesize array elements on the surface of a substrate. An array analogous to a dot or slot blot may also be used to arrange and link elements to the surface of a substrate using UV, chemical, thermal, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags, or fragments thereof may comprise the elements of the microarray. Fragments suitable for hybridization can be selected using software well known in the art such as LASERGENE software(DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

EXAMPLE 6

Complementary Polynucleotides

Sequences complementary to the LYG2-encoding sequences, or any parts thereof, are used to detect, decrease, or inhibit expression of naturally occurring LYG2. Although use of oligonucleotides comprising from about 15 to 30 base pairs is described, essentially the same procedure is used with smaller or with larger sequence fragments. LYG2 complementary oligonucleotides are designed using OLIGO 4.06 software. To inhibit transcription, a complementary oligonucleotide is designed from the most unique 5' sequence and used to prevent promoter binding to the coding sequence. To inhibit translation, a complementary oligonucleotide is designed to prevent ribosomal binding to the LYG2-encoding transcript.

EXAMPLE 7

Expression of LYG2

Expression and purification of LYG2 is achieved using bacterial or virus-based expression systems.

For expression of LYG2 in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express LYG2 upon induction with isopropyl beta-D-thiogalactopyranoside (IPTG). Expression of LYG2 in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding LYG2 by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, LYG2 is synthesized as a fusion protein with, e.g., glutathione S-transferase (GST) or a peptide epitope tag, such as FLAG, 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from LYG2 at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins. Methods for protein expression and purification are discussed in Current Protocols in Molecular Biology, John Wiley & Sons, New York, N.Y., ch 10, 16. Purified LYG2 obtained by these methods can be used directly in the following activity assay.

EXAMPLE 8

Demonstration of LYG2 Activity

LYG2 activity is demonstrated by the ability to lyse *Micrococcus lysodeikticus* bacterial cells. (Enzymatic Assay of Lysozyme 1, Sigma Aldrich, St. Louis Mo.). A 0.015% suspension of lyophilized *Micrococcus lysodeikticus* cells is prepared in 66 mM potassium phosphate buffer, pH 6.24 (Buffer A) at 25° C. 2.5 ml of the cell suspension is pipetted into a optical cuvette and equilibrated to 25° C. The absorbance at 450 nm is monitored until constant, between 0.6 and 0.7, using a thermostatted spectrophotometer. A blank reaction is prepared in a second cuvette containing 2.5 ml Buffer A. LYG2 is dissolved in cold Buffer A. 0.1 ml of the LYG2 solution is added to the test cuvette, and 0.1 ml Buffer A is added to the blank cuvette. The cuvettes are immediately mixed by inversion, and the decrease in absorbance at 450 nm is recorded for approximately 5 minutes. As the bacteria lyse, the turbidity of the solution, and hence the absorbance at 450 nm, decrease. The rate of the decrease in absorbance at 450 nm in the test cuvette was proportional to the amount of LYG2 in the original sample.

EXAMPLE 9

Functional Assays

LYG2 functions are assessed by transferring and expressing the sequences encoding LYG2 at physiologically elevated levels in mammalian cell culture systems. cDNA is subcloted into a mammalian expression vector containing a strong promoter that drives high levels of cDNA expression. Vectors of choice include PCMV SPORT (Life Technologies) and PCR 3.1 (Invitrogen, Carlsbad, Calif.), both of which contain the cytomegalovirus promoter. 5–10 ng of recombinant vector are transiently transfected into a human cell line, preferably of endothelial or hematopoietic origin, using either liposome formulations or electroporation. 1–2 ng of an additional plasmid containing sequences encoding a marker protein are co-transfected. Expression of a marker protein provides a means to distinguish transfected cells from nontransfected cells. Marker proteins of choice include, e.g., Green Fluorescent Protein (GFP), CD64, or a CD64-GFP fusion protein.

Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin to the cell surface. Methods in flow cytometry are discussed in Ormerod, M. G. (1994) Flow Cytometry, Oxford, New York, N.Y.

The influence of LYG2 on gene expression can be assessed using highly purified populations of cells transfected with sequences encoding LYG2 and CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding LYG2 and other genes of interest can be analyzed by Northern analysis or microarray techniques.

EXAMPLE 10

Production of LYG2 Specific Antibodies

LYG2 substantially purified using polyacrylamide gel electrophoresis (PAGE), or other purification techniques, is used to immunize rabbits and to produce antibodies using standard protocols. Alternatively, the LYG2 amino acid sequence is analyzed using LASERGENE software to determine regions of high immunogenicity, and a corresponding oligopeptide is synthesized and used to raise antibodies by means known to those of skill in the art. The appropriate epitopes, such as those near the C-terminus or in hydrophilic regions are selected using conventional methods in the art.

Typically, oligopeptides 15 residues in length are synthesized using an ABI model 43/A peptide synthesizer and coupled to (keyhole limpet haemocyanin) KLH by reaction with N-maleimidobenzoyl-N-hydroxysuccinimide ester (MBS) to increase immunogenicity. Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

EXAMPLE 11

Purification of Naturally Occurring LYG2 Using Specific Antibodies

Naturally occurring or recombinant LYG2 is substantially purified by immunoaffinity chromatography using antibodies specific for LYG2. An immunoaffinity column is constructed by covalently coupling anti-LYG2 antibody to an activated chromatographic resin, such as CNBr-activated SEPHAROSE resin (Amersham Pharmacia Biotech). After the coupling, the resin is blocked and washed according to the manufacturer's instructions.

Media containing LYG2 are passed over the immunoaffinity column, and the column is washed under conditions that allow the preferential absorbance of LYG2 (e.g., high ionic strength buffers in the presence of detergent). The column is eluted under conditions that disrupt antibody/LYG2 binding (e.g., a buffer of pH 2 to pH 3, or a high concentration of a chaotrope, such as urea or thiocyanate ion), and LYG2 is collected.

EXAMPLE 12

Identification of Molecules which Interact with LYG2

LYG2, or biologically active fragments thereof, are labeled with $^{125}$I. (See, e.g., Bolton et al. (1973) Biochem. J. 133:529–539.) Candidate molecules previously arrayed in the wells of a multi-well plate are incubated with the labeled LYG2, washed, and any wells with labeled LYG2 complex are assayed. Data obtained using different concentrations of LYG2 are used to calculate values for the number, affinity, and association of LYG2 with the candidate molecules.

Although the invention has been described in connection with specific preferred embodiments, it should be understood that the invention as claimed should not be unduly limited to such specific embodiments. Indeed, various modifications of the described modes and systems for carrying out the invention are intended to be within the scope of the following claims.

What is claimed is:

1. An isolated and purified polynucleotide encoding a polypeptide comprising the amino acid sequence of SEQ ID NO: 1.

2. An isolated and purified polynucleotide comprising the contiguous nucleotide sequence of nucleotides 1–846 or of nucleotides 114–662 of SEQ ID NO: 2.

3. An isolated and purified polynucleotide which is complementary to the polynucleotide of claim 1.

4. An expression vector comprising the polynucleotide of claim 1.

5. A host cell comprising the expression vector of claim 4.

6. A method for producing a polypeptide, the method comprising the steps of:
(a) culturing the host cell of claim 5 under conditions suitable for the expression of the polypeptide; and
(b) recovering the polypeptide from the host cell culture.

7. A method for detecting a polynucleotide encoding a polypeptide having lysozyme activity in a biological sample containing nucleic acids, the method comprising the steps of:
(a) hybridizing the polynucleotide of claim 3 to at least one of the nucleic acids of the biological sample under stringent conditions with a wash step in conditions of 15 mM NaCl, 1.5 mM trisodium citrate, and 0.1% SDS at a temperature of at least 68° C., thereby forming a hybridization complex; and
(b) detecting the hybridization complex, wherein the presence of the hybridization complex correlates with the presence of a polynucleotide encoding the polypeptide in the biological sample;

whereby the polynucleotide encoding a polypeptide having lysozyme activity is detected.

8. A method of screening a library of molecules or compounds to identify at least one molecule or compound which specifically binds a polynucleotide encoding a polypeptide comprising the amino acid sequence of SEO ID NO: 1 under stringent conditions, the method comprising the steps of:
(a) combining an isolated and purified polynucleotide encoding a polypeptide comprising the amino acid sequence of SEQ ID NO: 1 with a library of molecules or compounds under conditions to allow specific binding under stringent conditions with a wash step in conditions of 15 mM NaCl, 1.5 mM trisodium citrate, and 0.1% SDS at a temperature of at least 68° C.; and
(b) detecting specific binding;
thereby identifying a molecule or compound which specifically binds the polynucleotide.

9. An isolated and purified polypeptide comprising the amino acid sequence of SEQ ID NO:1.

* * * * *